(12) United States Patent
Glazier et al.

(10) Patent No.: US 9,592,039 B2
(45) Date of Patent: Mar. 14, 2017

(54) FILLED BALLOON ARTERIOTOMY LOCATOR FOR VASCULAR CLOSURE DEVICES AND METHODS

(75) Inventors: Valerie J. Glazier, Eden Prairie, MN (US); Scott A. Kramer, Minneapolis, MN (US); Catherine A. Pipenhagen, Plymouth, MN (US)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 140 days.

(21) Appl. No.: 14/116,284

(22) PCT Filed: May 15, 2012

(86) PCT No.: PCT/US2012/037877
§ 371 (c)(1),
(2), (4) Date: Dec. 10, 2013

(87) PCT Pub. No.: WO2012/158662
PCT Pub. Date: Nov. 22, 2012

(65) Prior Publication Data
US 2014/0088641 A1    Mar. 27, 2014

Related U.S. Application Data

(60) Provisional application No. 61/486,470, filed on May 16, 2011.

(51) Int. Cl.
*A61B 17/08* (2006.01)
*A61D 1/00* (2006.01)
*A61B 17/00* (2006.01)

(52) U.S. Cl.
CPC *A61B 17/0057* (2013.01); *A61B 2017/00637* (2013.01); *A61B 2017/00654* (2013.01); *A61B 2017/00867* (2013.01)

(58) Field of Classification Search
CPC .......... A61B 17/0057; A61B 17/00623; A61B 17/00637; A61B 17/00654;
(Continued)

(56) References Cited

U.S. PATENT DOCUMENTS 5,951,589 A    9/1999 Epstein et al.
6,045,569 A    4/2000 Kensey et al.
(Continued)

FOREIGN PATENT DOCUMENTS

WO    2011025529 A1    3/2011

OTHER PUBLICATIONS

PCT International Search Report for PCT International Patent Application No. PCT/US2012/037877, mailed Aug. 23, 2012.

*Primary Examiner* — Melanie Tyson
(74) *Attorney, Agent, or Firm* — Holland & Hart

(57) ABSTRACT

A tissue puncture locator device includes an anchor assembly and a sealing member. The anchor assembly includes an anchor portion, a tube portion, and a filling member. The anchor portion is positioned at a distal end of the tube portion and configured for placement through a vascular incision into a vessel. The anchor member has an unexpanded configuration that permits passage through the vascular incision and an expanded configuration that limits passage through the vascular incision. The filling member is retained in the tube portion and adapted for insertion from the tube portion into the anchor member to provide the expanded configuration, and adapted for retraction from the anchor member into the tube portion to provide the unexpanded configuration. The sealing member is configured for placement adjacent the vascular incision outside the vessel.

16 Claims, 20 Drawing Sheets

(58) Field of Classification Search
CPC .......... A61B 17/12022; A61B 17/1205; A61B 17/12159; A61B 17/00672
See application file for complete search history.

(56) References Cited

U.S. PATENT DOCUMENTS

| | | | |
|---|---|---|---|
| 6,090,130 A | 7/2000 | Nash et al. | |
| 6,699,261 B1 | 3/2004 | Cates et al. | |
| 6,932,830 B2* | 8/2005 | Ungs | A61F 2/013 606/200 |
| 2004/0176798 A1* | 9/2004 | Epstein | A61B 17/00491 606/213 |
| 2006/0034930 A1* | 2/2006 | Khosravi | A61B 17/00491 424/484 |

\* cited by examiner

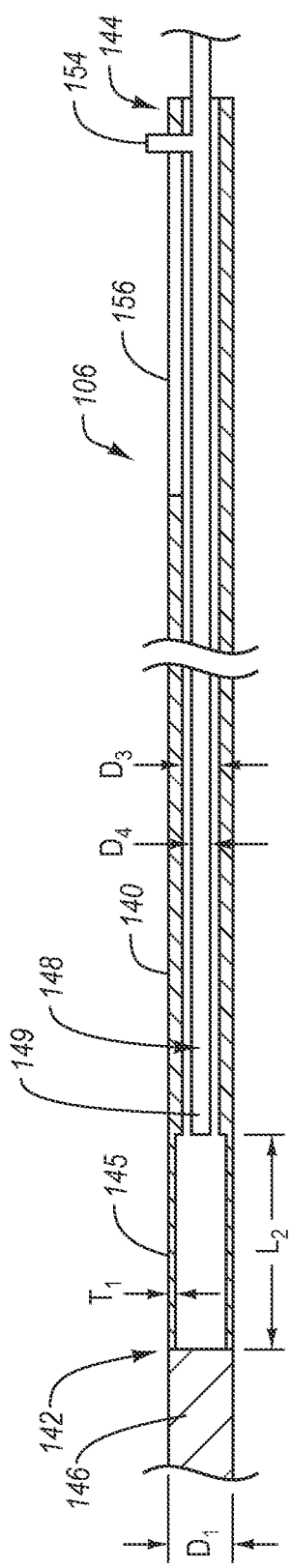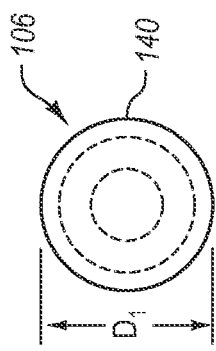

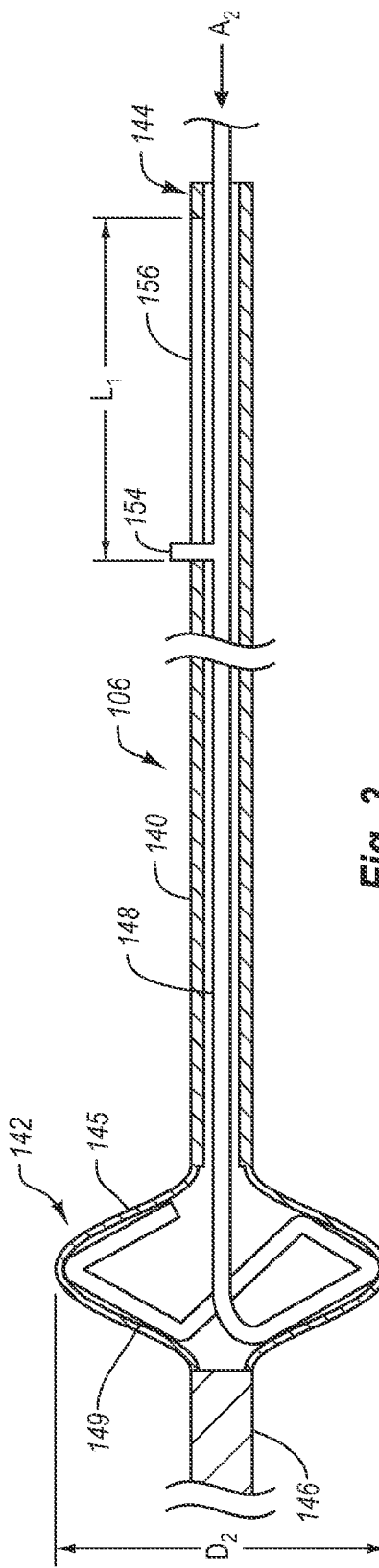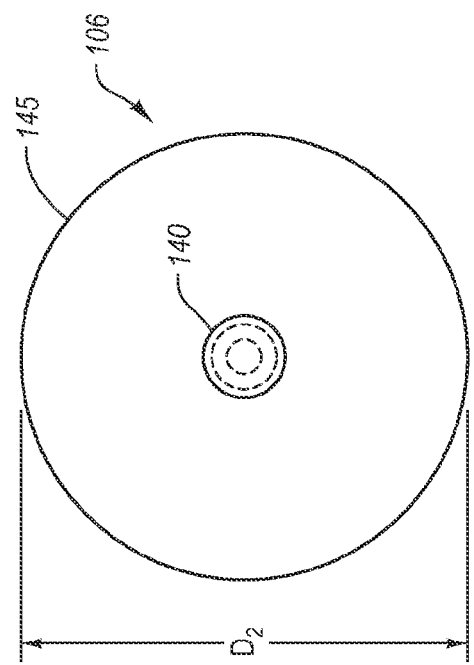
Fig. 3
Fig. 4

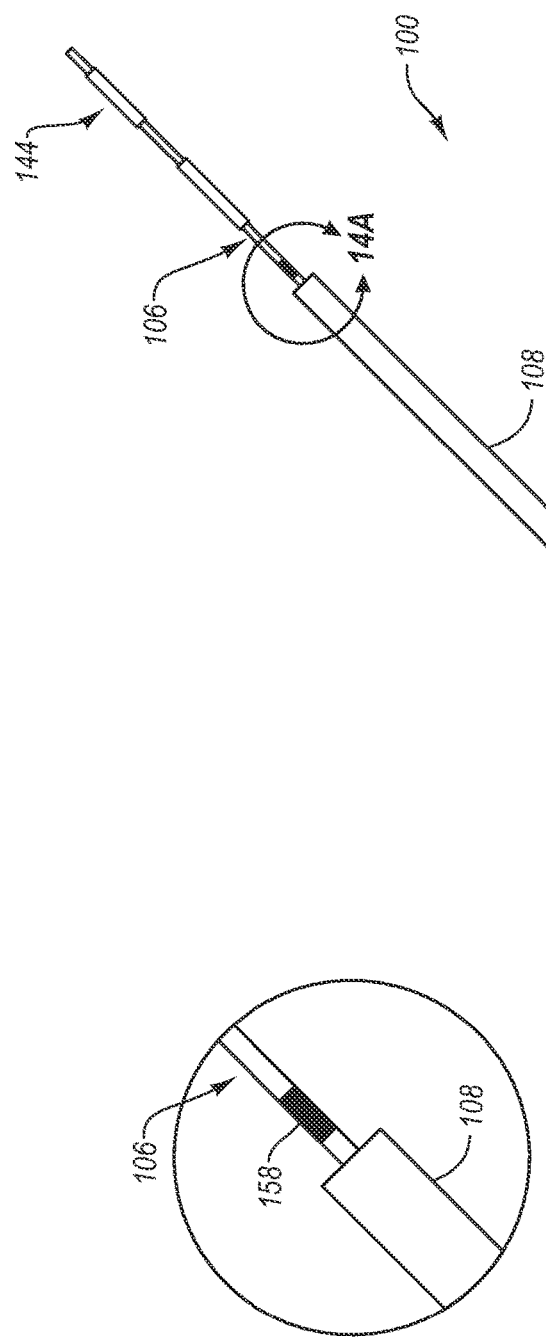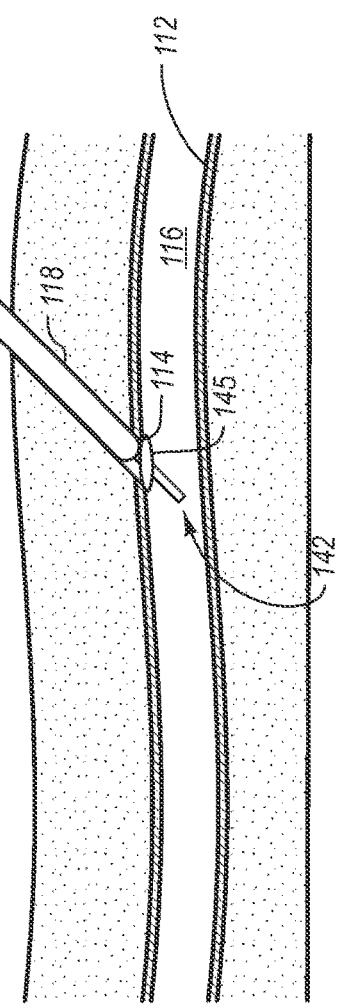
Fig. 14
Fig. 14A

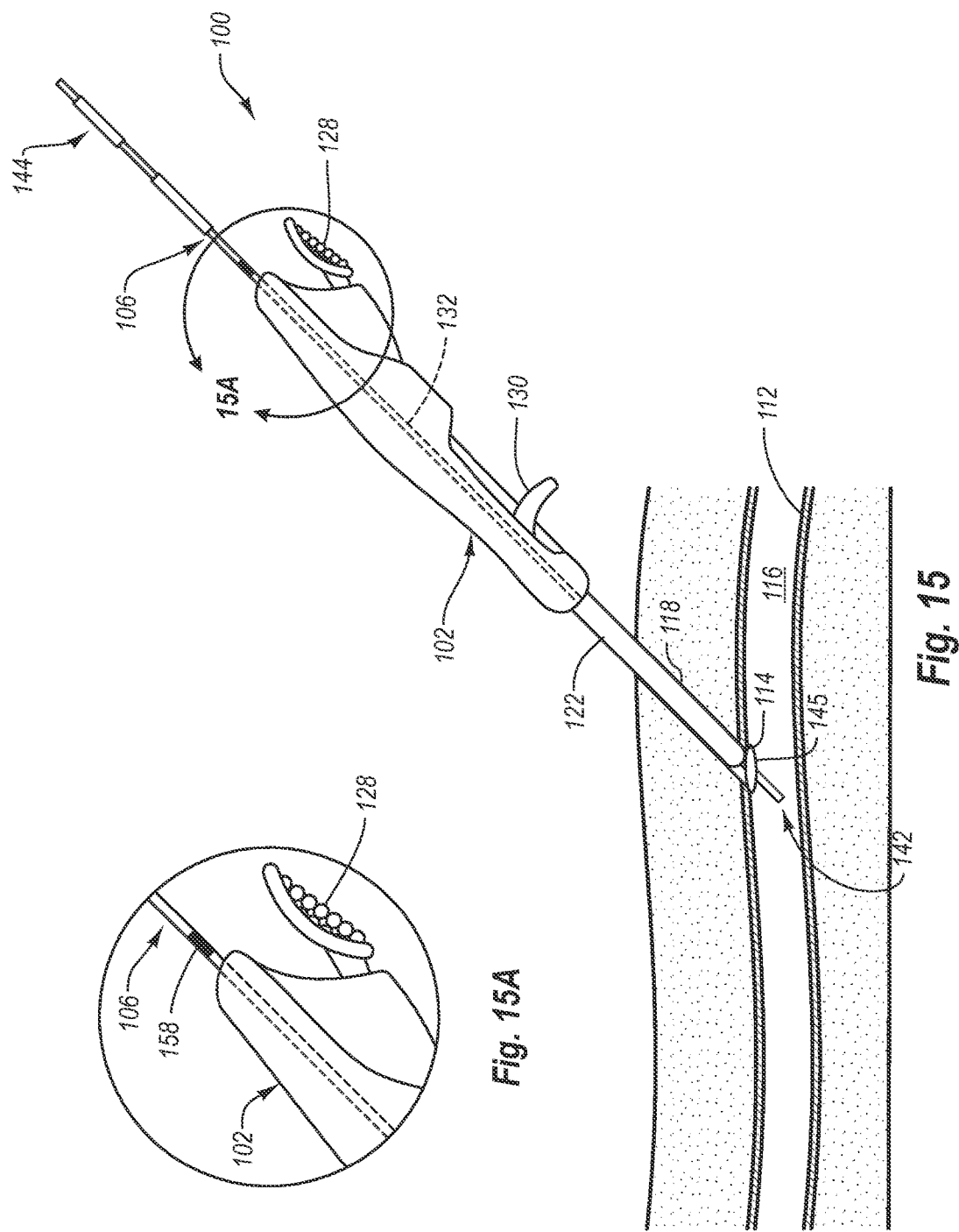

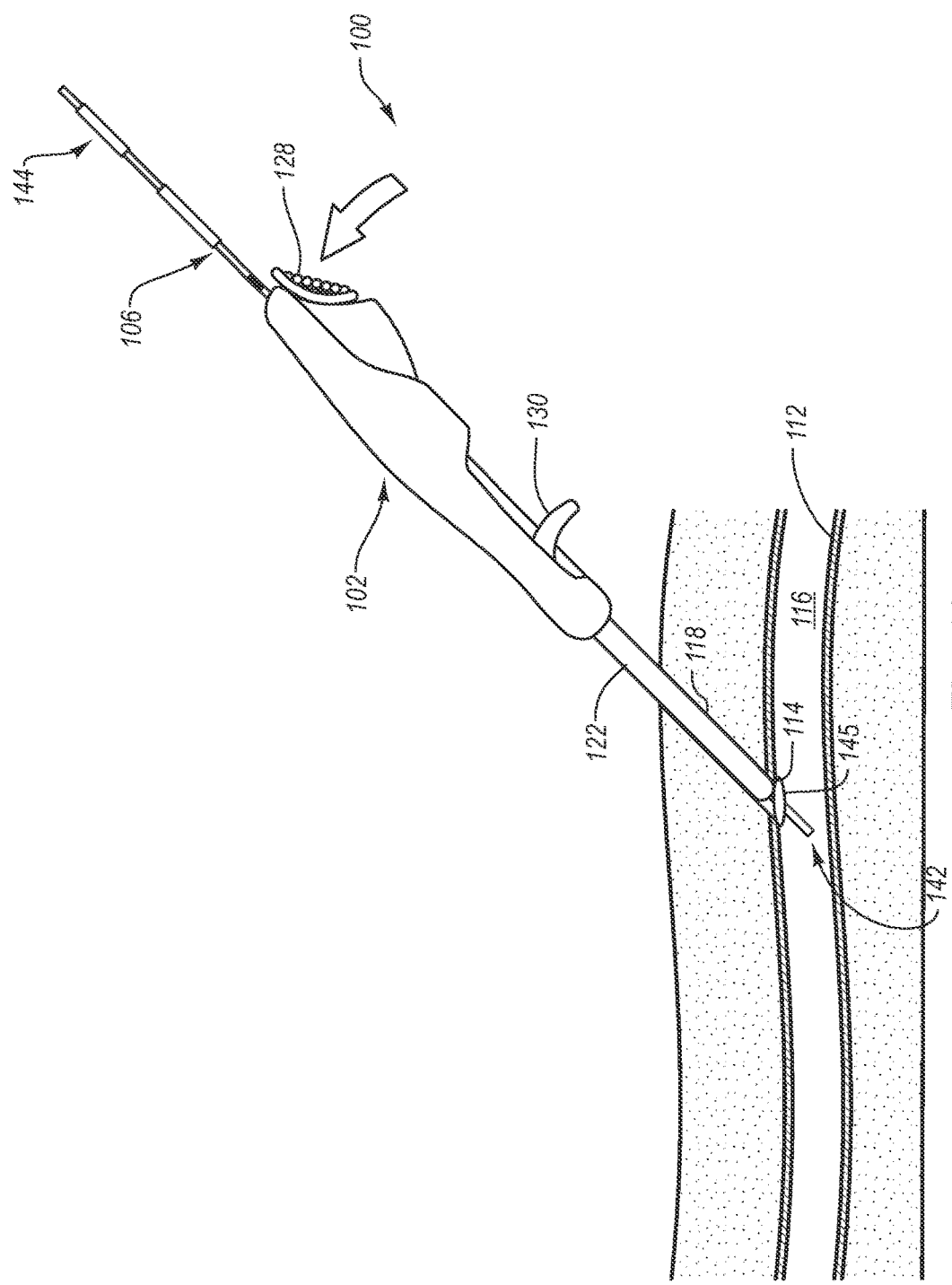

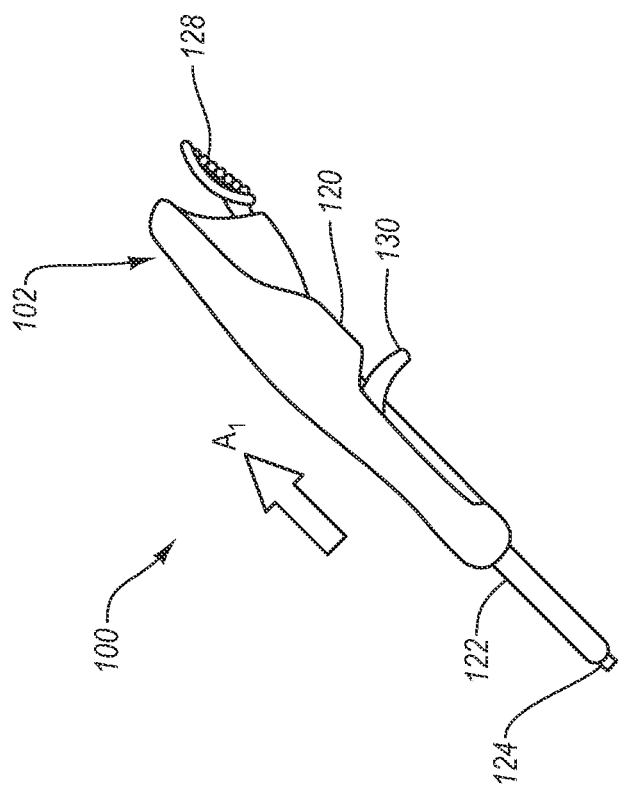
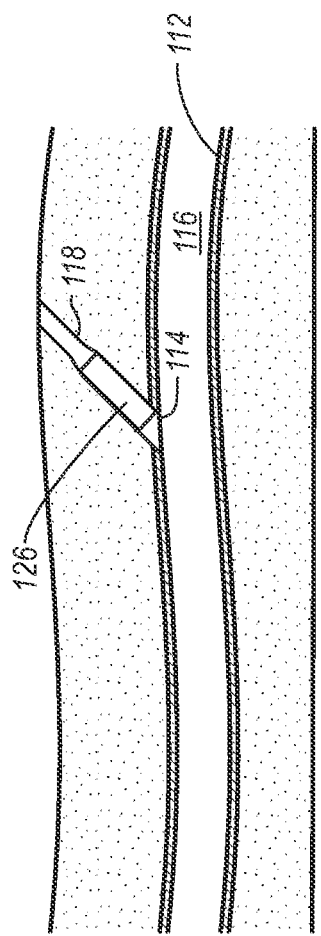
Fig. 22

FILLED BALLOON ARTERIOTOMY LOCATOR FOR VASCULAR CLOSURE DEVICES AND METHODS

RELATED APPLICATION

This claims the benefit of U.S. Provisional Application No. 61/486,470, filed 16 May 2011, which is hereby incorporated by reference herein in its entirety.

TECHNICAL FIELD

The present disclosure relates generally to medical devices and more particularly to vascular closure devices.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., a catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, may be stopped by utilizing vascular closure devices, such as those described in U.S. Pat. Nos. 6,090,130 and 6,045,569, which are hereby incorporated in their entireties by this reference.

Typical closure devices such as the ones described in the above-mentioned patents place a sealing plug at the tissue puncture site. Successful deployment of the sealing plug involves ejecting the sealing plug from within the closure device sheath to a location in alignment with and adjacent to the tissue puncture along an outer surface of the vessel. Misalignment of the sealing plug relative to the tissue puncture may result in improper sealing of the tissue puncture. Failure to contact the sealing plug against the outer surface of the vessel may also result in an improper seal.

SUMMARY

One aspect of the present disclosure relates to a tissue puncture locator device that includes an anchor assembly and a sealing member. The anchor assembly includes an anchor portion, a tube portion, and a filling member. The anchor portion is positioned at a distal end of the tube portion and configured for placement through a vascular incision into a vessel. The anchor member has an unexpanded configuration that permits passage through the vascular incision and an expanded configuration that limits passage through the vascular incision. The filling member is retained in the tube portion and adapted for insertion from the tube portion into the anchor member to provide the expanded configuration. The filling member is also adapted for retraction from the anchor member into the tube portion to provide the unexpanded configuration. The filling member may have a random arrangement within the anchor member. The sealing member is configured for placement adjacent to the vascular incision outside of the vessel. Typically, the anchor member may retract through the sealing member when in the unexpanded configuration.

The filling member may be selected from one of a wire member, a polymer strand, and a gel strand. The device may further include a handle portion, wherein the tube portion extends from the handle portion to the anchor portion. The sealing member may be movable along the tube member to a position adjacent to the vascular incision. The sealing member may comprise a collagen pad. The anchor assembly may further include an actuator configured to move the filling member into the anchor member and retract the filling member from the anchor member.

Another aspect of the present disclosure relates to a tissue puncture closure device that is adapted for insertion into and sealing of a tissue puncture in an internal tissue wall that is accessible through a percutaneous incision. The device includes an anchor, a filling material, and a sealing member. The anchor is disposed on a distal side of the internal tissue wall. The filling material is positioned in the tissue puncture closure device and movable from a first position removed from the anchor, to a second position inserted within the anchor to expand the anchor, and back to the first position. The filling material may have a random orientation in the second position. The sealing member is disposed on a proximal side of the internal tissue wall. The anchor is movable through the sealing member when the filling material is in the first position.

The device may further include an elongate shaft, wherein the anchor is positioned at a distal end of the elongate shaft and the filling material is positioned in the elongate shaft in the first position. The filling material may be shaped as an elongate structure. The filling material may maintain a solid or semi-solid state when in the first and second positions. The sealing member may include a collagen material. The device may further include a sheath, wherein the sealing member is positioned in the sheath before being disposed on the proximal side of the internal tissue wall. The device may also include a tamping member configured to advance the sealing member out of the sheath.

A further aspect of the present disclosure relates to a method of sealing a tissue puncture in an internal tissue wall that is accessible through a percutaneous incision. The method may include providing a tissue puncture closure device that includes an anchor portion, a filling member, and a sealing plug, inserting the anchor portion through the tissue puncture to a distal side of the tissue puncture, and moving the filling member into the anchor portion to expand the anchor portion to a size sufficient to resist movement of the anchor member proximally through the tissue puncture. The filling member may have a random arrangement within the anchor portion and a linear configuration when removed from the anchor portion. The method may further include disposing the sealing plug in the percutaneous incision adjacent a proximal side of the tissue puncture, moving the filling member out of the anchor portion to reduce a size of the anchor portion, and withdrawing the anchor portion through the tissue puncture and sealing plug.

The filling member may be a solid or semi-solid member, and moving the filling member into the anchor portion includes maintaining a cross-sectional shape and size of the filling member. Moving the filling member may include advancing the filling member distally from a first position in the tissue puncture closure device to a second position at least partially positioned in the anchor portion. The tissue puncture closure device may further include a shaft portion, and moving the filling member out of the anchor portion includes positioning the filling member in the shaft portion.

The filling member may be one of a wire structure, a polymeric strand structure, and a gel strand structure. Moving the filling member into or out of the anchor portion may include actuating an actuator mechanism to advance and retract the filling member. Disposing the sealing plug may include compressing the sealing plug against the internal tissue wall. The tissue puncture closure device may also include an actuator that is connected to the filling material, and moving the filling material includes actuating the actuator to move the filling material in a proximal direction or a distal direction.

Additional advantages and novel features will be set forth in the description which follows or can be learned by those skilled in the art through reading these materials or practicing the examples disclosed herein. The advantages of the invention can be achieved through the features recited in the attached claims.

BRIEF DESCRIPTION OF THE DRAWINGS

The accompanying drawings illustrate various embodiments of the present disclosure and are a part of the specification. The illustrated embodiments are merely examples and do not limit the scope of the invention.

FIG. 1 is a cross-sectional side view of a portion of an example locator wire assembly in accordance with the present disclosure with an expandable member in an unexpanded state.

FIG. 2 is an end view of the locator wire assembly of FIG. 1.

FIG. 3 is a cross-sectional side view of the locator wire assembly of FIG. 1 with the expandable member in an expanded state and a filling member in a first configuration.

FIG. 4 is an end view of the locator wire assembly of FIG. 3.

FIGS. 9 and 9A are side views of the tissue puncture treatment assembly of FIG. 8 with the locator wire assembly inserted into the introducer and into the vessel.

FIGS. 10 and 10A are side views of the tissue puncture treatment assembly of FIG. 9 with a filling member of the locator wire assembly being distally advanced to expand an expandable portion of the locator wire assembly within the vessel.

FIGS. 11 and 11A are side views of the tissue puncture treatment assembly of FIG. 10 with the locator wire assembly being retracted to engage the expandable portion against a distal end of the introducer.

FIGS. 12 and 12A are side views of the tissue puncture treatment assembly of FIG. 11 with the introducer and locator wire assembly being retracted to engage the expandable portion against an interior wall of the vessel.

FIGS. 13 and 13A are side views of the tissue puncture treatment assembly of FIG. 12 with the introducer removed.

FIGS. 14 and 14A are side views of the tissue puncture treatment assembly of FIG. 13 with a tissue tract dilator advanced over the locator wire assembly and into the percutaneous incision.

FIGS. 15 and 15A are side views of the tissue puncture treatment assembly of FIG. 14 with the tissue tract dilator removed and a sealing pad delivery device advanced over the locator wire assembly and into the percutaneous incision.

FIG. 16 is a side view of the tissue puncture treatment assembly of FIG. 15 with the sealing pad delivery device locked onto the locator wire assembly.

FIGS. 20 and 20A are side views of the tissue puncture treatment assembly FIG. 19 with the locator wire assembly being actuated to move the filling member proximally to permit the expandable portion to return to an unexpanded state.

FIG. 22 is a side view of the tissue puncture treatment assembly of FIG. 21 with the sealing pad delivery device removed from the percutaneous incision.

Throughout the drawings, identical reference numbers designate similar, but not necessarily identical, elements.

DETAILED DESCRIPTION

Figure 5:
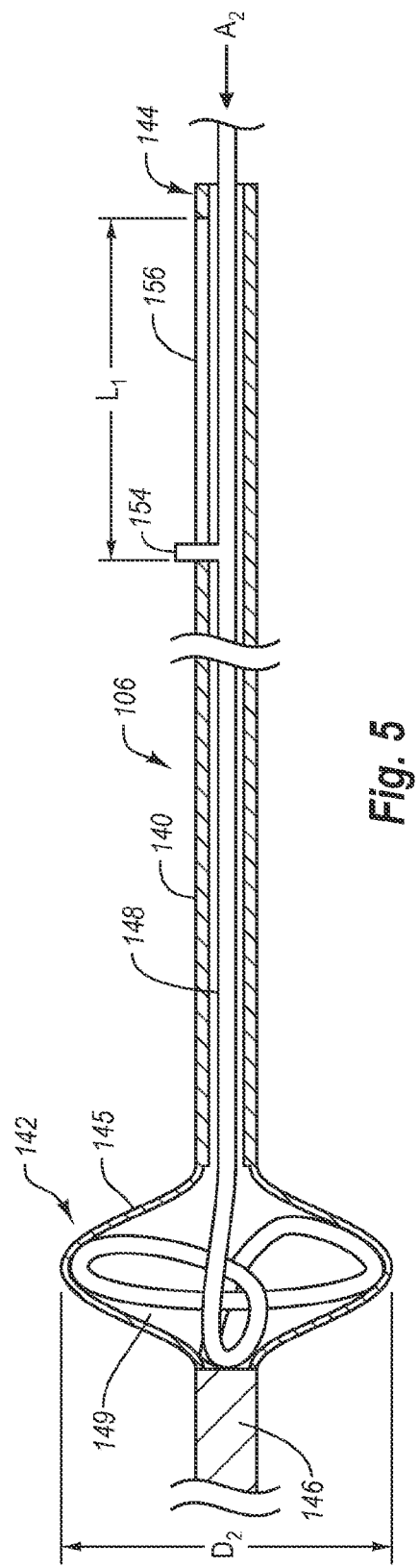
FIG. 5 is a cross-sectional side view of the locator wire assembly of FIG. 1 with the expandable member in an expanded state and the filling member in a second configuration.

As mentioned above, vascular procedures are conducted throughout the world and require access to an artery through a puncture. Most often, the artery is a femoral artery. To close the puncture following completion of the procedure, many times a closure device is used to position a sealing plug within a percutaneous incision adjacent to the puncture. Orientation of the sealing plug relative to the puncture may be particularly useful for successful sealing of the puncture.

Compressing the sealing plug against the puncture typically improves sealing of the puncture. In order to apply a compressing force to the sealing plug, it is helpful to provide an anchor positioned within the vessel on an opposite side of the vascular wall from the sealing plug. The anchor may be pulled proximally against the vessel wall as the sealing member is compressed or advanced generally in the distal direction to create a seal against the outer surface of the vessel in the area adjacent to the puncture.

An anchor positioned within the vessel may also provide a sealing function for the puncture prior to disposing the sealing plug adjacent to the puncture. The anchor may be constructed and positioned within the vessel to at least partially block or occlude a flow of blood through the puncture. Some types of anchors for use with closure devices are constructed as an inflatable balloon. The anchor, once positioned in the vessel, is filled with a gas or liquid from a source of fluid that is coupled to the vascular closure device. Fluid-filled balloon anchors may pose a risk of bursting while in the vessel, which could cause serious complications for the patient. Further, connecting the source of fluid to the closure device for use in filling the balloon adds substantial complexity and size to the closure device that may limit ease of use for the operator.

Other types of anchors include a metal cage or basket construction that is expandable within a balloon membrane. Typically, the cage structure is maintained within the balloon membrane at all times during use of the closure device. When the anchor is positioned within the vessel, the cage structure is expanded to expand the balloon membrane. The anchor is retracted to a position against an inner wall of the vessel. The cage structure is moved to its original unexpanded position after the sealing plug is properly deployed on an opposite side of the vessel wall. Such cage structures are typically complex mechanical devices that require costly manufacturing and assembly processes.

While the vascular instruments shown in the attached figures and described below include procedural sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the term "engage" and "engagable" are also used broadly to mean interlock, mesh, or contact between two devices. Likewise "disengage" or "disengagable" means to remove or capable of being removed from interlock, mesh, or contact. A "tube" is an elongated device with a passageway. The passageway may be enclosed or open (e.g., a trough). A "lumen" refers to any open space or cavity in a bodily organ, especially in a blood vessel. The words "including" and "having," as used in the specification, including the claims, have the same meaning as the word "comprising."

FIGS. 1-5 illustrate an example locator wire assembly 106 for use with a tissue puncture treatment assembly 100 as will be described in further detail below. The locator wire assembly 106 (also referred to herein as a "locator wire" or a "wire assembly") includes a locator tube 140, a distal end portion 142, a proximal end portion 144, a stop or plug member 146, and an expandable portion 145 positioned at the distal end portion 142. The locator wire assembly 106 further includes a filling member 148 (also referred to herein as a "strand" or a "strand member") that is positioned within the locator tube 140 and is movable into and out of the expandable portion 145. The filling member 148 is typically operable from a location proximal of the expandable portion 145 and is axially movable relative to the locator tube 140. Typically, the filling member 148 is moved axially a predetermined distance to fill and expand the expandable portion 145, and to retract from and permit return of the expandable portion 145 to an unexpanded state.

Referring to FIG. 1, the locator wire assembly 106 is shown with the expandable portion 145 in an unexpanded state. The expandable portion 145 has a maximum diameter or dimension $D_1$. Typically, the dimension $D_1$ is smaller than a minimum internal dimension of an introducer into which the expandable portion 145 is inserted, and smaller than a minimum size of a vessel incision through which the locator wire assembly 106 is inserted, as will be described below with reference to FIGS. 8-22. The filling member 148 is shown spaced proximal of the expandable portion 145. In other arrangements, a distal end portion 149 of the filling member 148 may be at least partially positioned within the expandable portion 145 prior to advancing the filling member 148 to expand the expandable portion 145.

The locator wire assembly 106 may include a follower member 154 that moves within a track 156 defined in the locator tube 140. The follower member 154 is typically coupled to the filling member 148 so that restrictions in axial movement of the follower member 154 relative to the track 156 corresponds to restrictions in axial movement of the filling member 148 relative to locator tube 140. In some arrangements (not shown in the figures), the filling member 148 may extend along only a portion of the length of the locator tube 140 (e.g., from the expandable portion 145 proximally to a location distal of the track 156), and an extension or actuator portion is connected to and extends proximally from the filling member 148. Such an extension or actuator portion may include the follower member 154 extending radially outward through the track 156.

In some arrangements, an internal dimension or diameter $D_3$ of the locator tube 140 is substantially greater than an outer diameter or dimension $D_4$ of the filling member 148 as shown in FIG. 1. Alternatively, the internal dimension $D_3$ may be similar in size to the dimension $D_4$. In one example, the dimension $D_3$ is in the range of about 100 percent to about 200 percent of the dimension $D_4$. More closely matching the size of the dimensions $D_3$, $D_4$ may help promote axial movement of the filling member 148 within the locator tube 140 without the filling member 148 buckling while being advanced into and retracted from the expandable portion 145.

FIGS. 3 and 4 illustrate the locator wire assembly 106 with the filling member 148 advanced distally into the expandable portion 145. A distal end portion 149 of the filling member 148 collects within the expandable portion 145 in a configuration that promotes radially outward expansion of the expandable portion 145 to a dimension $D_2$.

As the filling member 148 is advanced distally, the distal end portion 149 engages the plug 146 and begins to bend into a random, contorted configuration or orientation. Further distally advancing the filling member 148 increases the greater the radially outward force applied by the filling member 148 within the expandable portion 145. Typically, the greater the radially outward force applied by filling member 148, the further radially outward the expandable portion 145 expands. While the configuration of the filling member 148 within the expandable portion 145 is typically random (i.e., has no preformed shape or configuration), it may be possible to consistently provide the diameter $D_2$ within a certain range of sizes by advancing the filling member 148 distally a predetermined distance (i.e., a distance defined by a length $L_1$ of the track 156). In some examples, the dimension $D_2$ is in a range of 1 to about 8 millimeters and more preferably in a range of about 2 to 4 millimeters.

The axial length of movement of the filling member 148 to provide the diameter $D_2$ may vary depending on a number of factors such as, for example, the material composition, cross-sectional size, and a cross-sectional shape of the filling member 148. Other features include the unexpanded size $D_f$, wall thickness $T_1$ (see FIG. 1), length $L_2$, and material composition of the expandable portion 145.

In one example, the length of filling member 148 that is inserted into the expandable portion 145 is in the range of about 0.5 to about 5 centimeters, and more preferable in the range of about 1 to about 3 centimeters. The length $L_1$ of the track 156 may correlate directly with the length of filling member 148 that is inserted into the expandable portion 145 to provide the dimension $D_2$.

FIG. 5 illustrates another configuration or orientation of the filling member 148 within the expandable portion 145. The comparison of FIGS. 3 and 5 illustrates at least in part how the same filling member 148 may bend and contort into various shapes and configurations within the expandable portion 145 to provide expansion of the expandable portion 145 to the dimension $D_2$.

Figure 6:
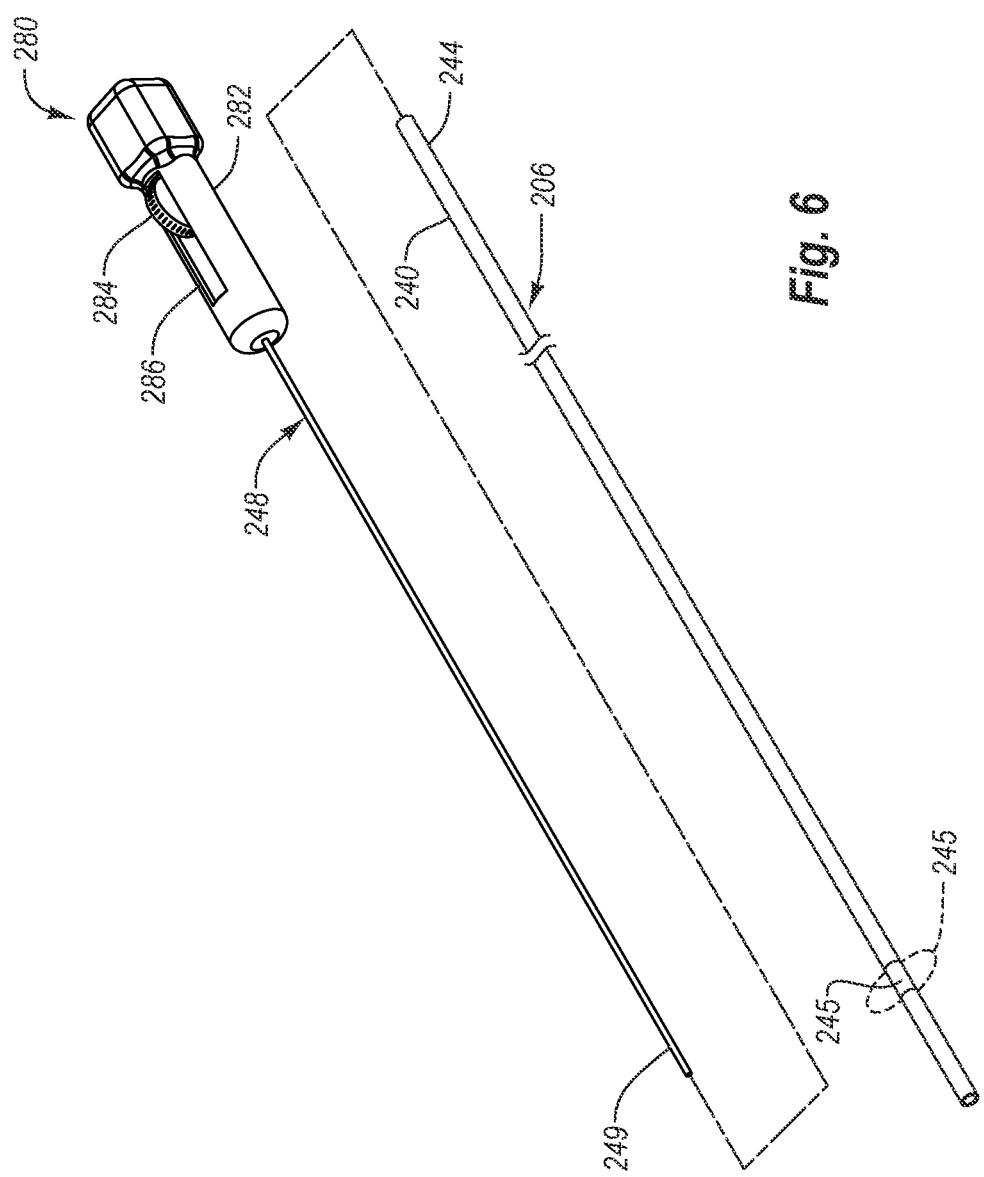
FIG. 6 is a partially exploded perspective view of another example locator wire assembly in accordance with the present disclosure.

The filling member 148 may be advanced and retracted relative to the locator 140 using various actuator devices in place of or in addition to the follower 154 and track 156. FIG. 6 illustrates a filling member actuator 280 that advances and retracts a filling member 248. The filling member actuator 280 includes a housing 282, an actuator 284, and an actuator track 286 within which the actuator 284 is operable. The actuator 284 is coupled to the filling member 248 such that operation of the actuator 284 within the actuator track 286 advances or retracts the filling member 248 relative to the housing 282. The actuator 284 may be configured as a scroll member. The scroll member may directly or indirectly contact the filling member 248 to axially move the filling member 248.

A distal end 249 of the filling member 248 may be inserted into a proximal end portion 244 of a locator tube 240 of a locator wire assembly 206. With the filling member 248 positioned within the locator tube 240 and the actuator 284 positioned proximally within the actuator track 286, an expandable portion 245 of the locator wire 206 is provided in an unexpanded state shown in solid lines. Advancing the filling member 248 in the distal direction by advancing the actuator 284 within the actuator track 286 causes the distal end 249 of the filling member 248 to collect within an expandable portion 245. The expandable portion 240 expands in the radially outward direction as the filling member 248 is advanced distally (i.e., see the expandable portion 245 in the broken line in FIG. 6). Retraction of the filling member 248 by moving the actuator 284 proximally in the actuator track 286 removes the filling member 248 from within the expandable portion 245 at least an amount sufficient to permit the expandable portion 245 to return to the unexpanded state shown in solid line in FIG. 6. Typically, the filling member 248 remains within the locator tube 240 prior to expanding the expandable portion 245 and after the expandable portion 245 has returned to an unexpanded state.

Figure 7:
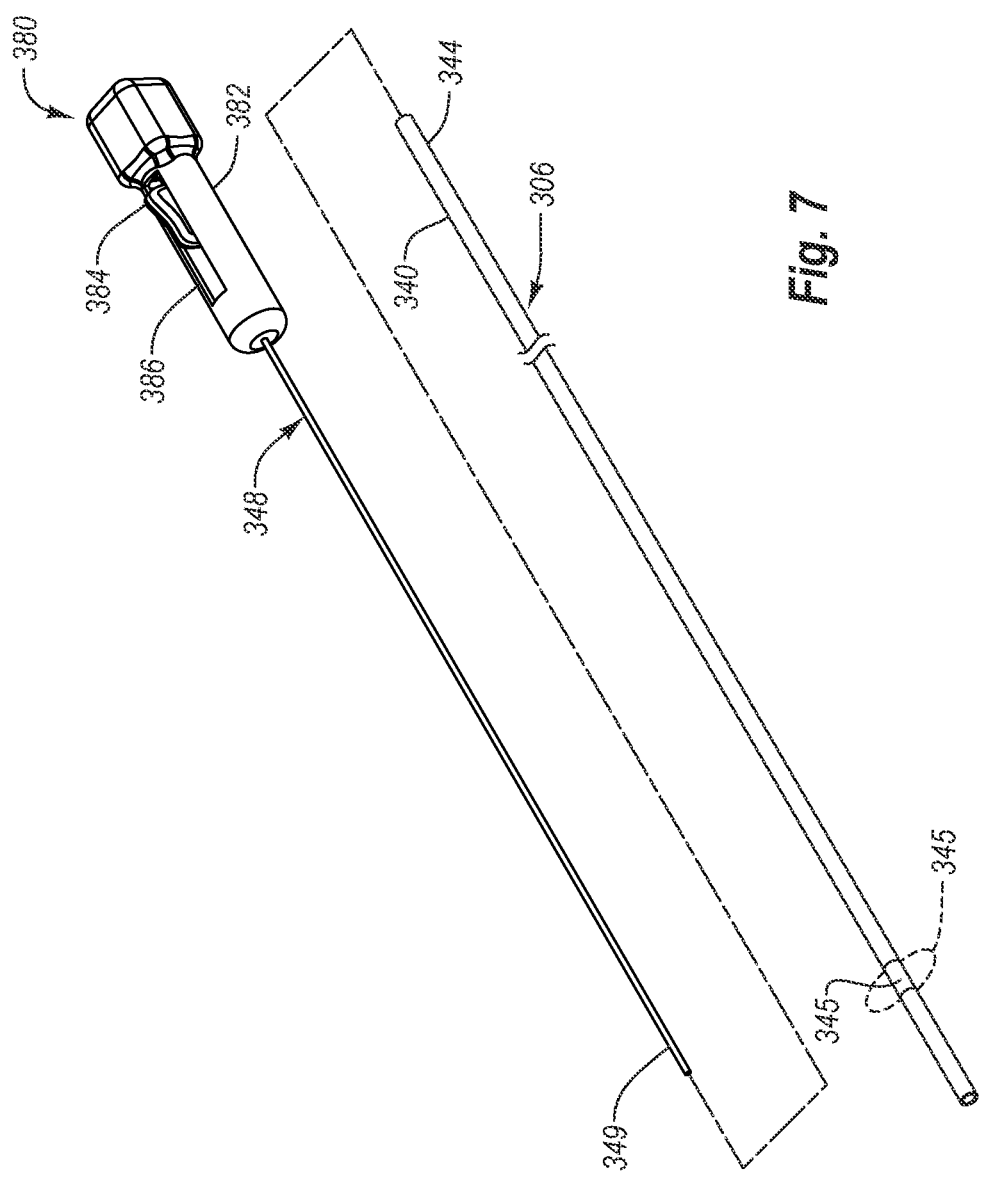
FIG. 7 is a partially exploded perspective view of another example locator wire assembly in accordance with the present disclosure.

FIG. 7 illustrates another example filling member actuator 380 that includes a housing 382, an actuator 384, and a filling member 348. The housing 382 includes an actuator track 386 within which the actuator 384 operates. The filling member 348 has a distal end 349 that is insertable into a distal end portion 344 of a locator tube 340 of a locator wire assembly 306.

The actuator 384 is configured as a thumb actuator wherein the operator applies a radially inward and axial force to the actuator 384 to move the actuator 384 within the track 386. After positioning the filling member 348 within the locator tube 340, the actuator 384 may be advanced distally within the track 386 to fill and expand an expandable portion 345 from an unexpanded state shown in solid lines in FIG. 7 to an expanded state shown in broken lines in FIG. 7.

The example filling members 148, 248, 348 described above and shown in the attached figures may comprise various materials. In one example, the filling member includes a metal material such as stainless steel or Nitinol. Nitinol may be particularly useful because of its elastic properties that provide return to an original shape after being deformed. In one example, the original shape of the filling member may be the generally elongate linear shape when positioned in the locator tube, and the deformed shape is whatever random shape the filling member takes when collected within the expandable portion.

Other materials suitable for the filling member may include, for example, semi-solid or solid gel materials, polymers, and coil structures of various material composition.

Referring now to FIGS. 8-22, an example tissue puncture treatment assembly 100 is described with reference to treatment of a vessel puncture 114. The tissue puncture treatment assembly 100 includes a sealing pad delivery device 102, an introducer 104, a locator wire assembly 106 (i.e., the locator wire assembly 106 described above with reference to FIGS. 1-5), and a tissue tract dilator 108. The tissue puncture treatment assembly 100 is used to seal closed a vessel puncture 114 in a vessel 112. The vessel 112 includes a vessel interior 116. The vessel puncture 114 is accessible from outside a patient via a percutaneous incision 118.

Figure 8:
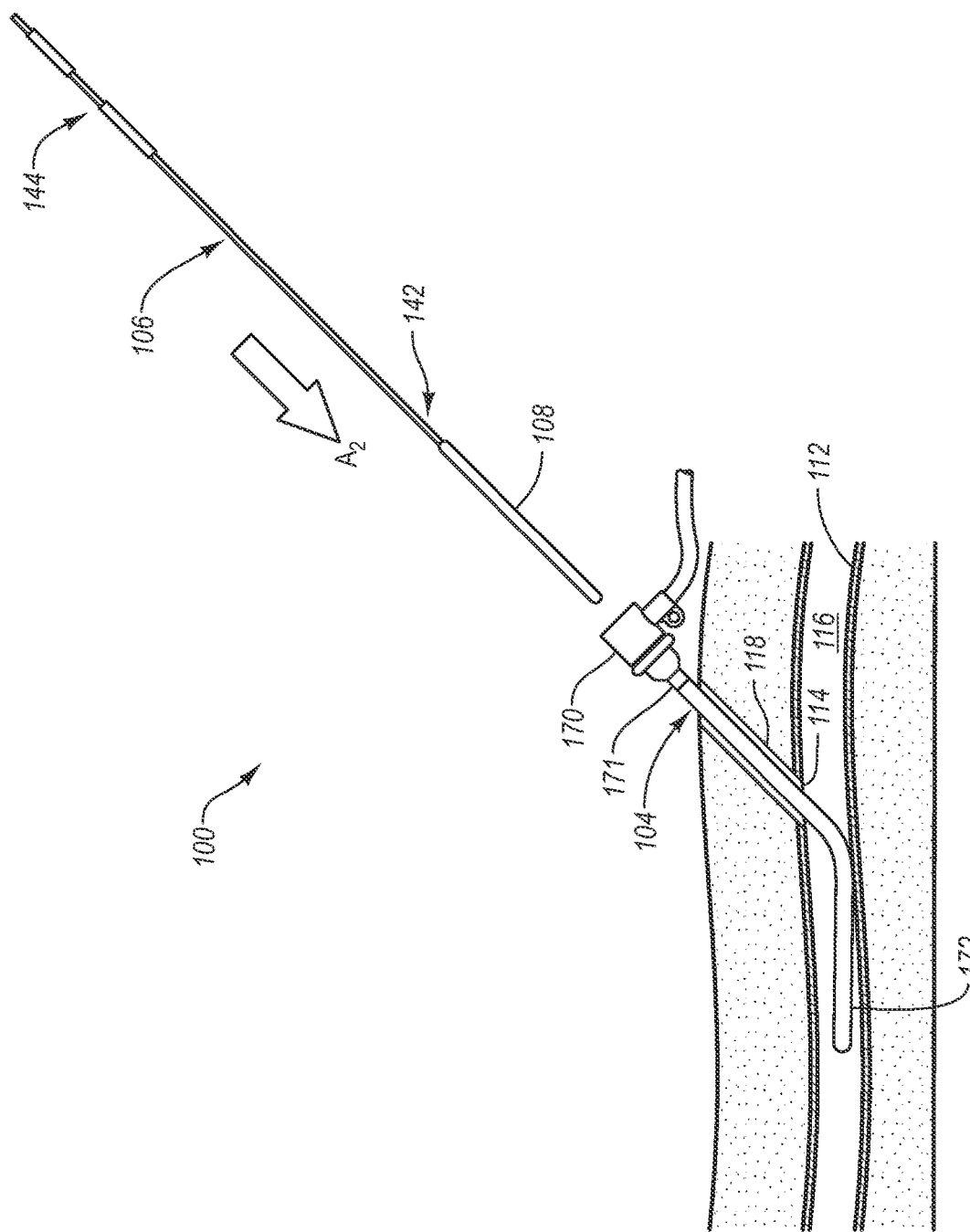
FIG. 8 is a side view of an example tissue puncture treatment assembly in accordance with the present disclosure, wherein an introducer is inserted into a vessel and a locator wire assembly is positioned for insertion into the introducer.

Referring first to FIG. 8, the introducer 104 is inserted through the percutaneous incision 118 and vessel puncture 114 until a distal end 172 of the introducer 104 is positioned within the vessel interior 116. A hub 170 is positioned at proximal end 171 of the introducer 104. The hub 170 defines an opening into the introducer through which the locator wire assembly 106 is advanced. The locator wire assembly 106 includes a distal end portion 142 and a proximal end portion 144. Typically, the distal end portion 142 is advanced through the hub 170 until the distal end portion 142 (including the expandable portion 145) extends distally beyond the distal end 172 of the introducer.

The tissue tract dilator 108 may be advanced into the introducer 104 concurrently with advancement of the locator wire assembly 106 into the introducer 104. Alternatively, the tissue tract dilator 108 may be advanced prior to or after insertion of the locator wire assembly 106 into the introducer 104. In some arrangements, the tissue tract dilator 108 may be advanced over the locator wire assembly 106 after the locator wire assembly has been advanced into the vessel 112.

Figure 9:
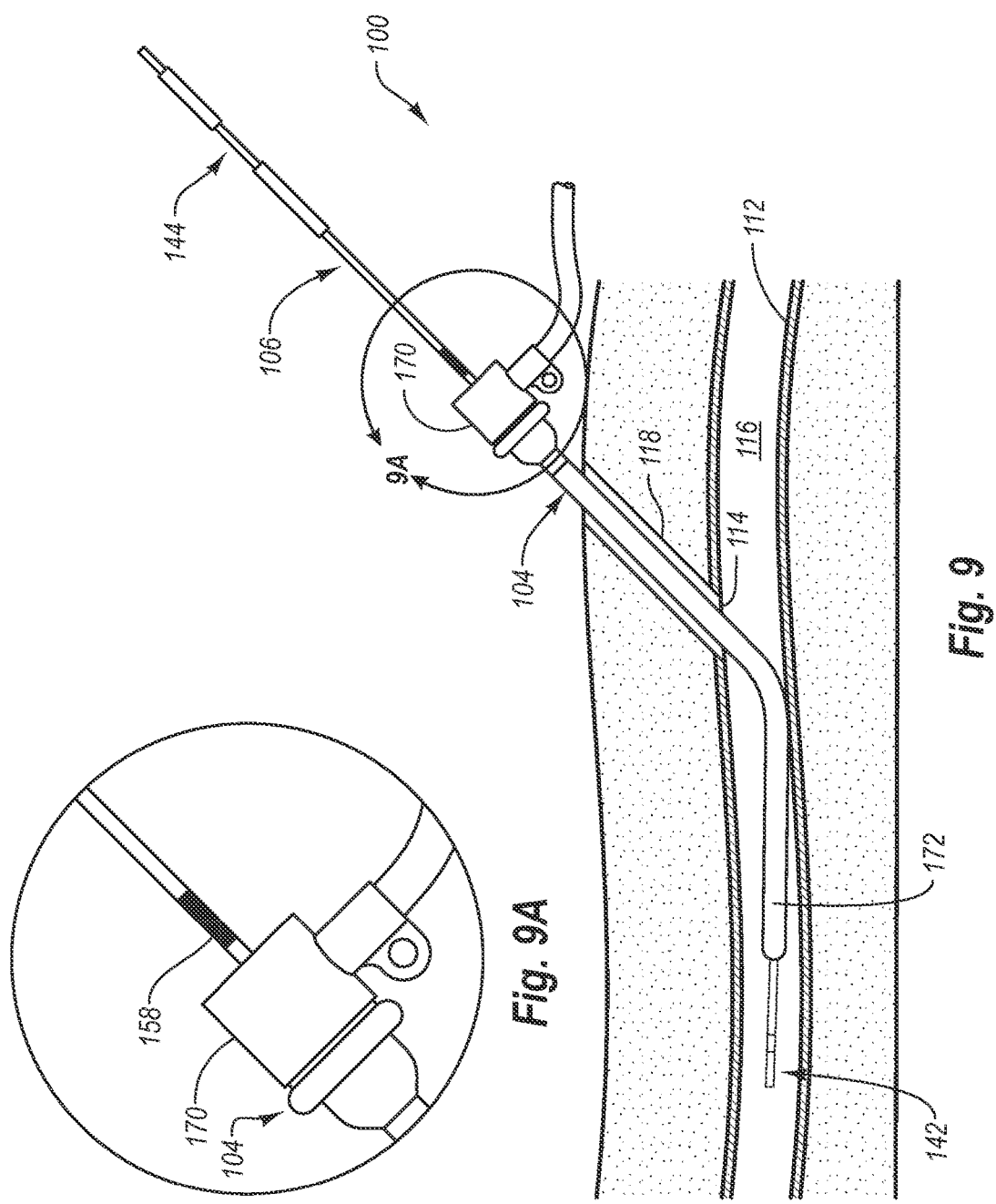

Referring now to FIGS. 9 and 9A, the locator wire assembly 106 is advanced distally through the introducer 104 until the distal end portion 142 is positioned within the vessel interior 116 at a location distal of the distal end 172 of the introducer. Proper positioning of the distal end portion 142 may be confirmed by visualizing a first marker 158 at a location adjacent to the hub 170, as shown in FIG. 9A.

Figure 10:
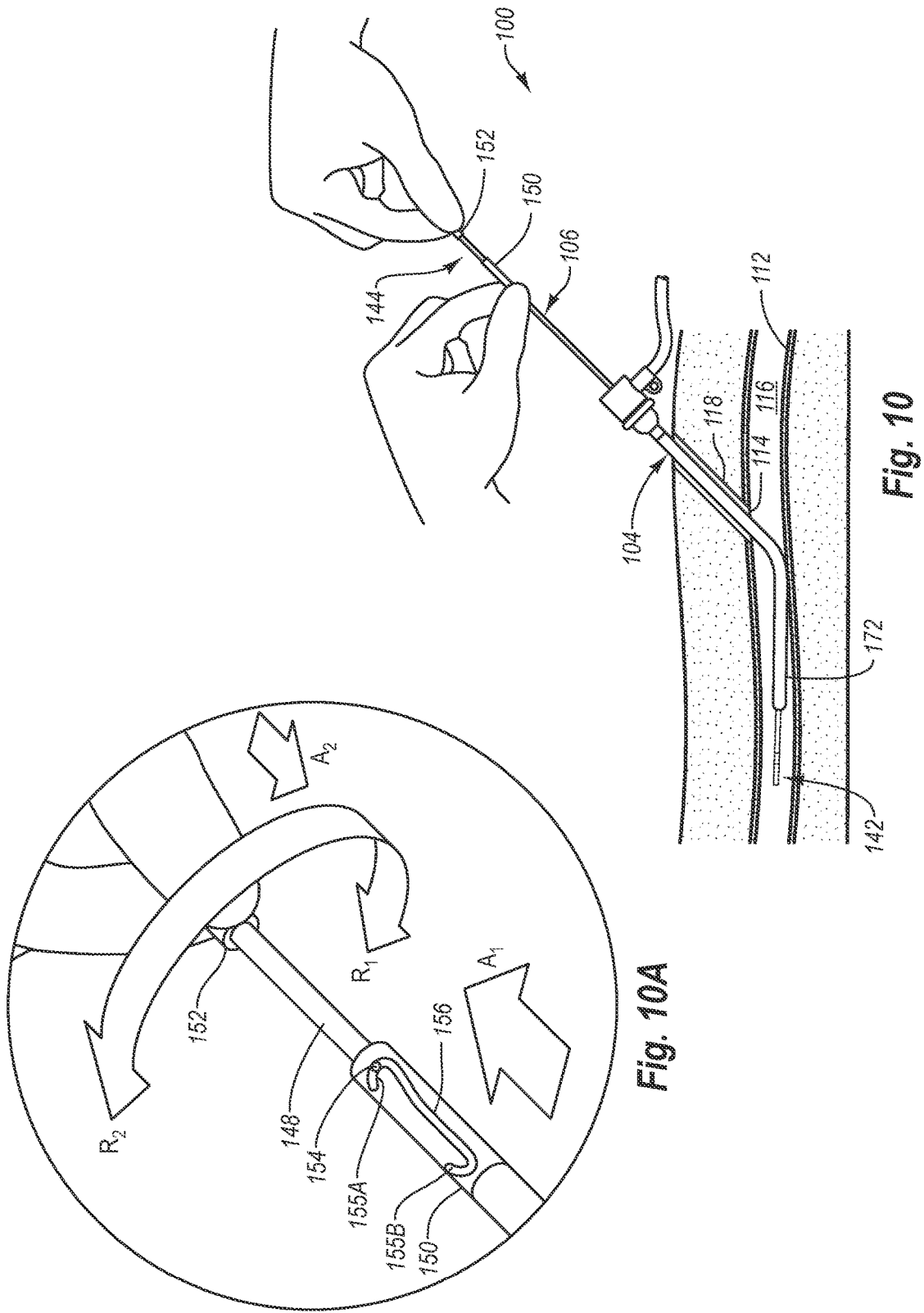

Referring now to FIGS. 10 and 10A, the locator 106 is actuated to compress the expandable portion 145 into a radially outward expanded state. In one example, the locator wire assembly 106 includes a filling member 148 that is positioned within a locator tube 140 and is movable into and out of the expandable portion 145. A first grasping member 150 may be positioned at a proximal end of the locator tube 140, and a second grasping member 152 is positioned at proximal end of the filling member 148. A follower member 158 extends from an outer surface of the filling member 148.

The follower member 154 moves within a track 156 that is defined in an outer surface of the tube member 140. The track 156 includes a proximal locking portion 155A and a distal locking portion 155B.

The operator rotates the filling member 148 relative to the tube member 140 in the direction $R_1$ to move the follower 154 out of the locking portion 155A of the track 156. The operator then applies an axial force in the direction $A_1$ via the first grasping member 150 while applying a force in the opposite direction $A_2$ to the filling member 148 via the second grasping member 152. When the follower member 154 reaches the distal end of the track 156, the operator applies a rotational force in the direction $R_2$ to move the follower member 154 into locking portion 155B of the track 156.

Figure 11:
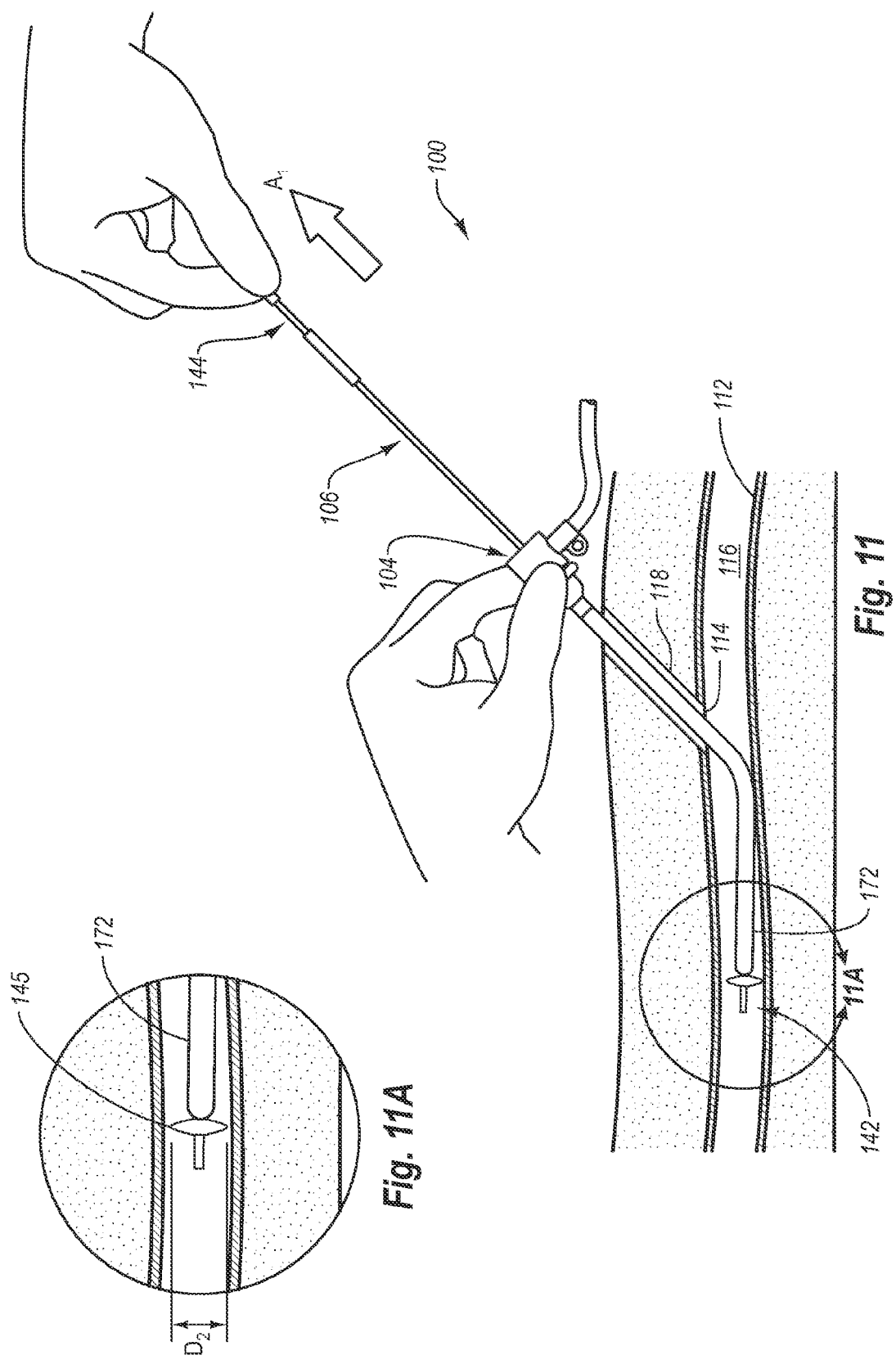

Applying the axial compression forces shown and described with reference to FIGS. 10 and 10A causes the filling member 148 to move into and expand the expandable portion 145 radially outward as shown in FIGS. 11 and 11A. Typically, the filling member 148 is randomly arranged in the expandable portion 145 as discussed above with reference to FIGS. 3 and 5. The expandable portion 145 has a maximum diameter or width dimension $D_2$ when in the expanded state shown in FIG. 11A. Typically, the dimension $D_2$ is greater than a maximum width dimension of the vessel puncture 114. The dimension $D_2$ is also typically greater than an internal dimension of the introducer 104 at the distal end 172 of the introducer 104.

Referring to FIGS. 11 and 11A, the operator applies a retraction force to locator wire assembly 106 in the proximal direction $A_1$ to contact the expandable portion 145 against a distal end surface of the introducer 104.

Figure 12:
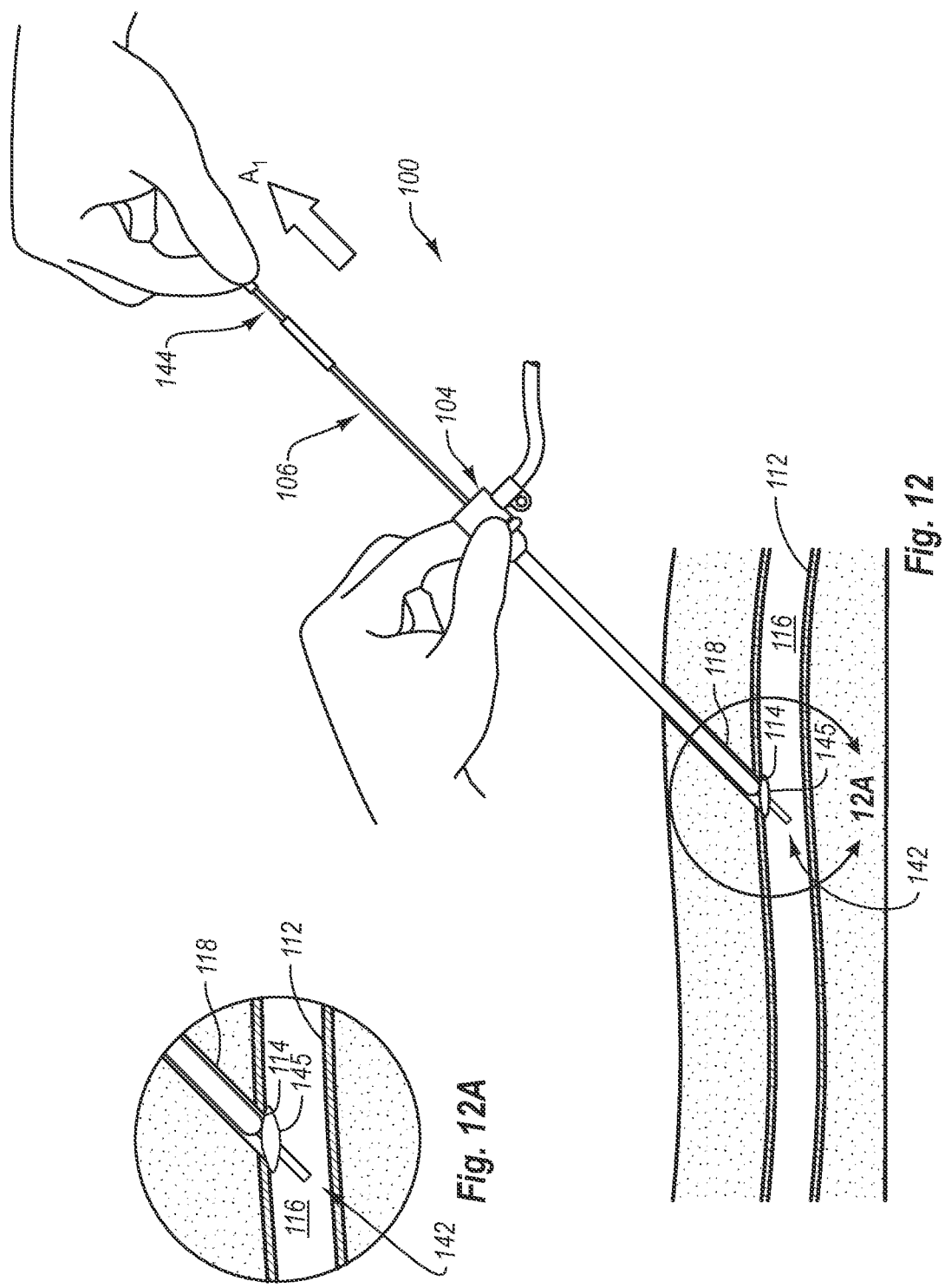

Referring to FIGS. 12 and 12A, the operator retracts the introducer 104 and locator wire assembly 106 in the direction $A_1$ until the expandable portion 145 contacts against an inner surface of the vessel 112 adjacent to the vessel puncture 114. Typically, the expandable portion 145 provide hemostasis at the vessel puncture 114. The operator may feel a slight resistance to retraction in the direction $A_1$ once the expanded expandable portion 145 contacts against the inner surface of the vessel 112.

Figure 13:
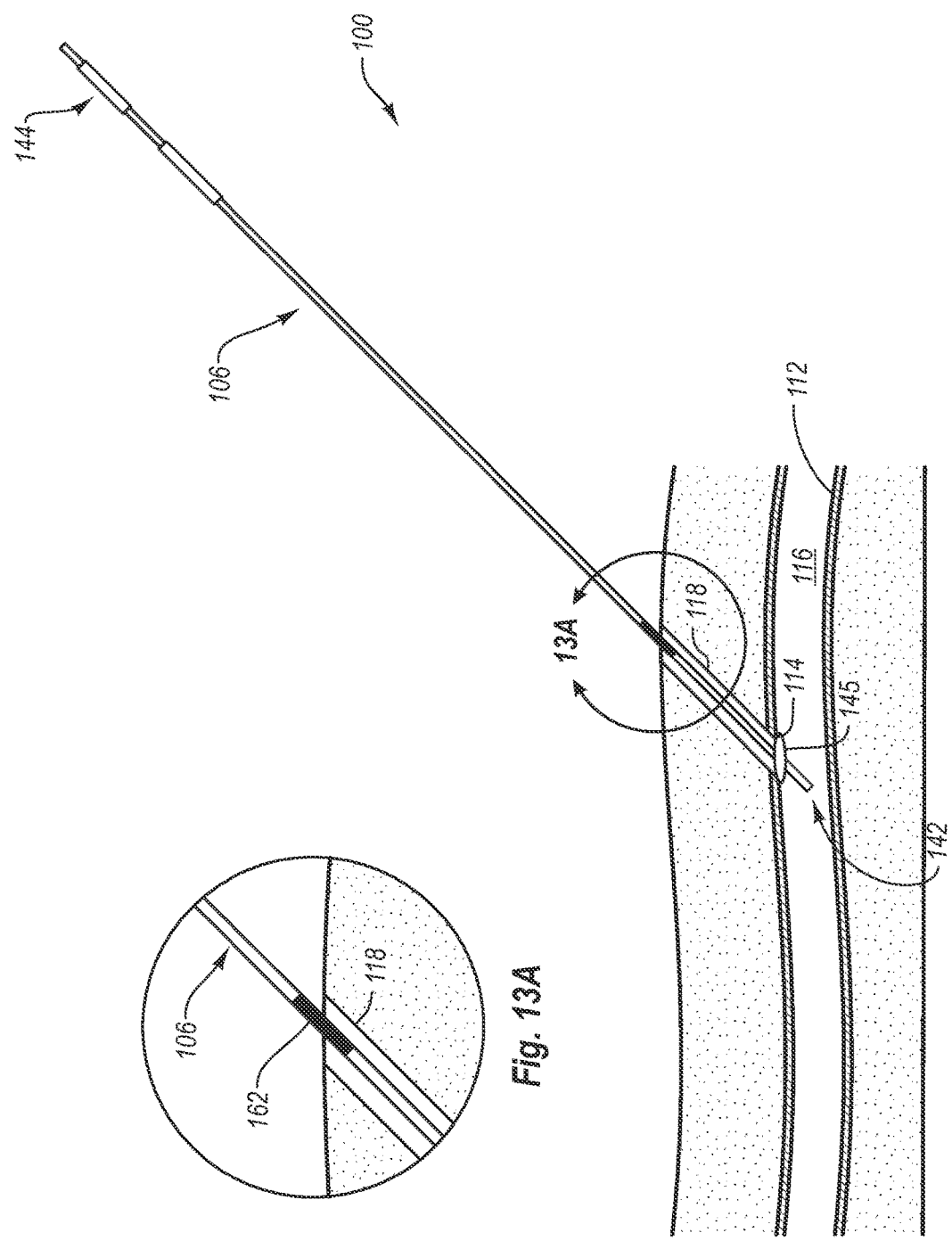

Referring to FIGS. 13 and 13A, the operator maintains at least some tension on the locator wire assembly 106 in the direction $A_1$ to maintain hemostasis while removing the introducer 104 in direction $A_1$ from off the locator wire assembly 106. A second marker 162 is usually at least partially visible outside of the percutaneous incision 118 after removal of the introducer 104.

Referring now to FIGS. 14 and 14A, a tissue tract dilator 108 may be advanced distally over the locator wire assembly 106 and into the percutaneous incision 118. The tissue tract dilator 108 may be advanced distally until the first marker 158 is at least partially visible outside a proximal end of the tissue tract dilator 108. At least some tension is usually applied to the locator wire assembly 106 to maintain hemostasis during advancement of the tissue tract dilator 108 into the percutaneous incision 118. The tissue tract dilator 108 may be used in some circumstances when the size or shape of the percutaneous incision 118 is not sufficient for placement of a sealing pad or positioning of the sealing pad delivery device 102.

Referring now to FIGS. 15 and 15A, the tissue tract dilator 108 is removed from percutaneous incision 118 and off from the locator wire assembly 106 in the direction $A_1$. At least some tension is typically applied to the locator wire assembly 106 in the proximal direction $A_1$ while removing the tissue tract dilator 108 to maintain hemostasis. The sealing pad delivery device 102 is then advanced distally over the locator wire assembly 106 and into the percutaneous incision 118. In at least some arrangements, the sealing pad delivery device 102 is advanced distally in the direction $A_2$ until the first marker 158 is at least partially visible at a location proximal of the sealing pad delivery device 102.

The sealing pad delivery device 102 includes a housing 120, a carrier tube 122 extending from a distal end of the housing 120, a positioning tube 124 positioned within the carrier tube 122, and a sealing pad or plug 126 positioned within the carrier tube 122. The sealing pad 126 is located distal of the positioning tube 124. The sealing pad delivery device 102 may also include a wire locking member 128, a tube retracting actuator 130, and a wire aperture 132. The wire aperture 132 extends from a proximal end of the housing 120 to a distal end of the carrier tube 122. The wire aperture 132 defines a path through which the locator wire assembly 106 passes.

Referring now to FIG. 16, once the sealing pad delivery device 102 is positioned within the percutaneous incision 118 with the first marker 158 at least partially visible and tension being applied to the locator wire assembly 106, the wire locking member 128 is actuated to fix an axially position of the sealing pad delivery device 102 relative to the locator wire assembly 106. In at least one example, the wire locking member 128 contacts the locator wire assembly 106 directly with a force sufficient to limit movement of the sealing pad delivery device 102 in the axial direction relative to the wire assembly 106 when applying forces that are typical in treating a vessel puncture 114. Many constructions are possible for the wire locking member 128 to provide the desired resistance to relative movement between the sealing pad delivery device 102 and the locator wire assembly 106.

Figure 17:
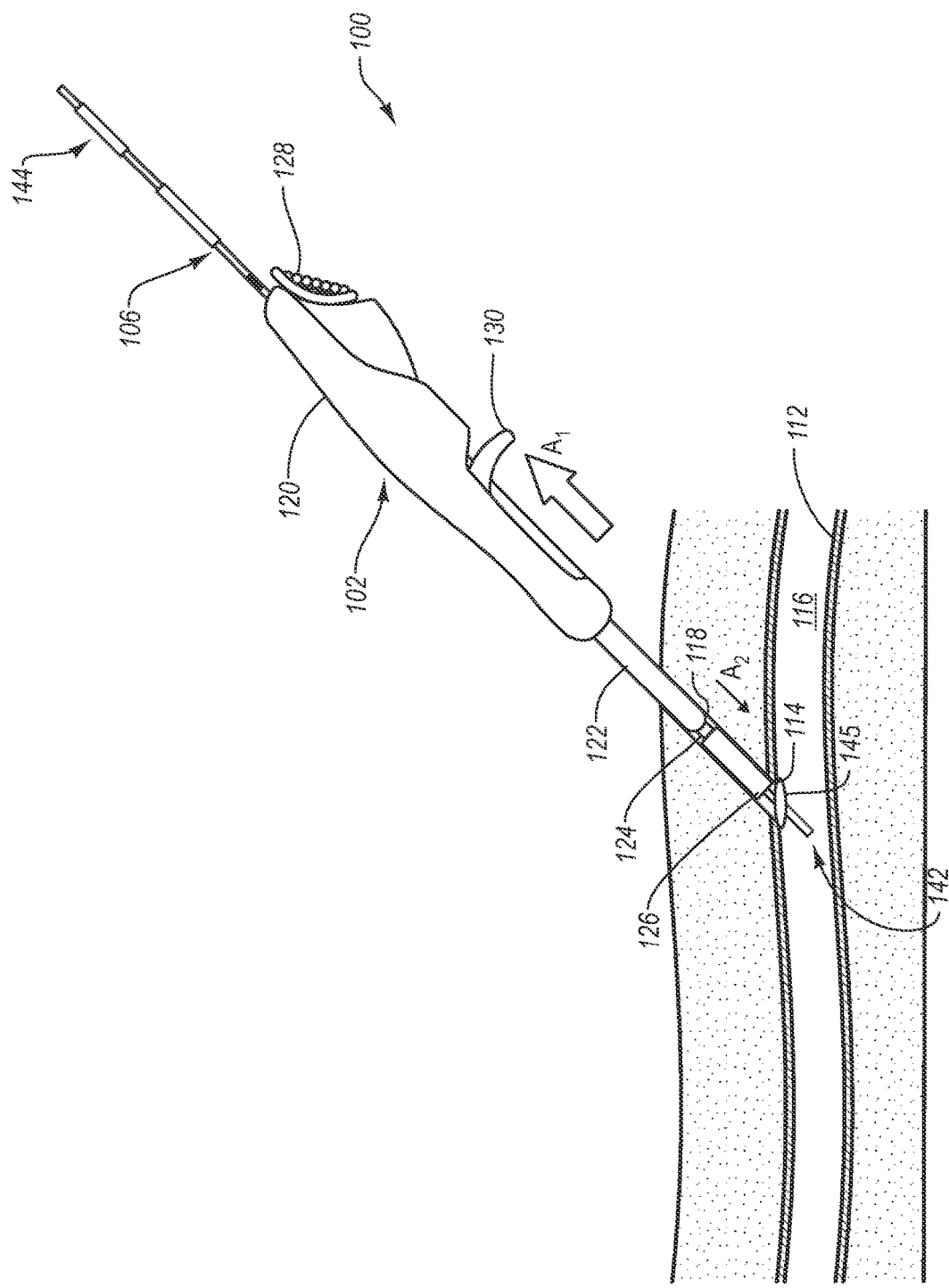
FIG. 17 is a side view of the tissue puncture treatment assembly of FIG. 16 with the sealing pad delivery device actuated to expose a sealing pad within the percutaneous incision.

Referring now to FIG. 17, a force is applied to the retraction actuator 130 in the proximal direction $A_1$ to retract the carrier tube 122 at least partially into the housing 120. Typically, the carrier tube 122 is retracted with the tube retractor actuator 130 a distance sufficient to fully expose the sealing pad 126 within the percutaneous incision 118.

In at least some arrangements, exposing the sealing pad 126 within the percutaneous incision 118 also advances the sealing pad 126 at least partially in the distal direction $A_2$. In one example, the positioning tube 124 may be used to distally advance and compress the sealing pad 126. In other arrangements, the positioning tube 124 limits proximal movement of the sealing pad during retraction of the carrier tube 122.

The expandable portion 145, held in contact with the inner surface of the vessel 112 adjacent to the vessel puncture 114, may provide an anchor that resists axial forces applied to the sealing pad 126 in the distal direction $A_2$. The anchor function of expandable portion 145 limits movement of the sealing pad 126 through the vessel puncture 114 and may facilitate at least some compression of the sealing pad 126 toward the vessel puncture 114. The expandable portion 145 may be referenced herein as an anchor or anchor member.

Figure 18:
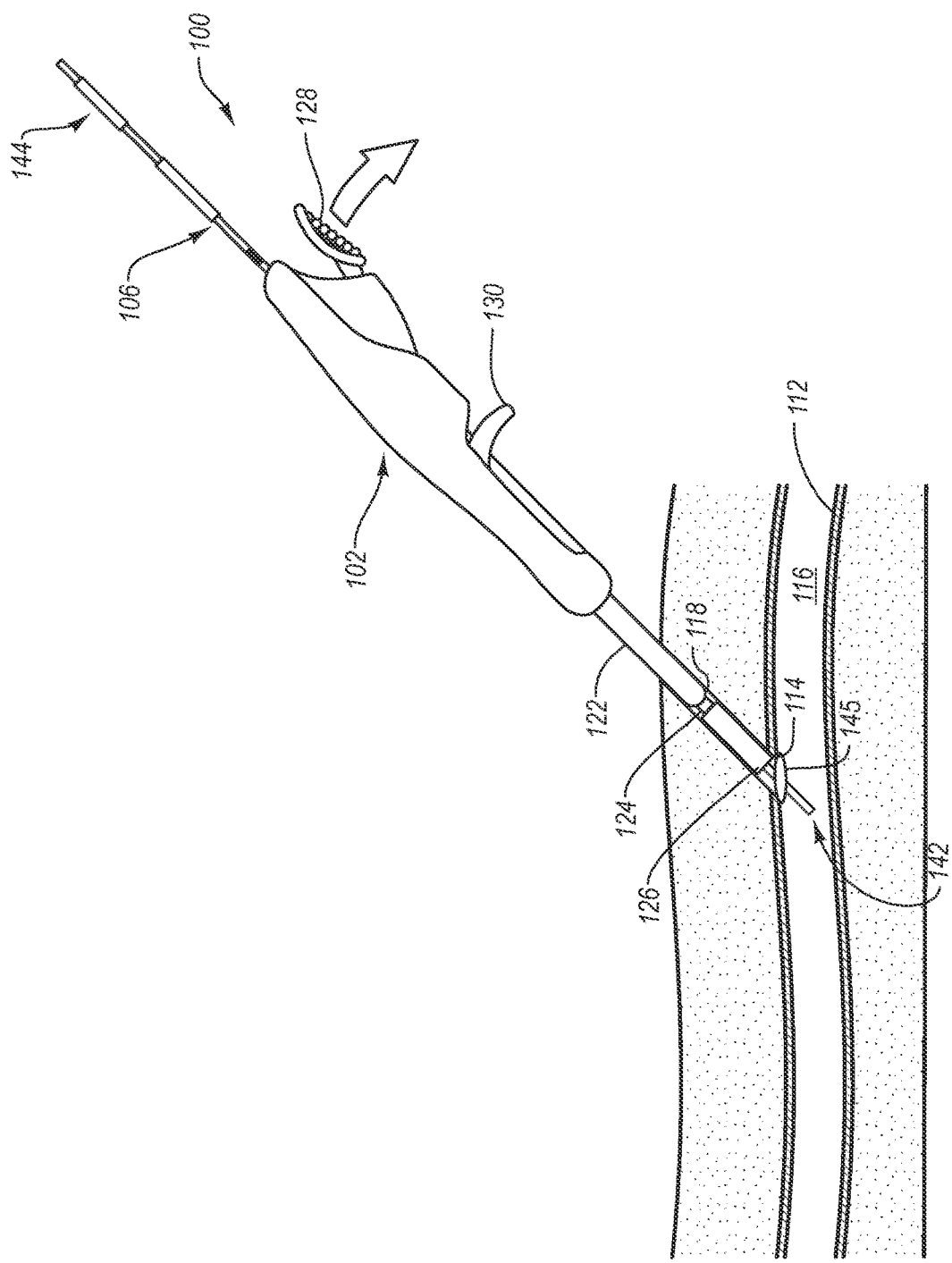
FIG. 18 is a side view of the tissue puncture treatment assembly of FIG. 17 with the sealing pad delivery device released from the locator wire assembly.
Figure 19:
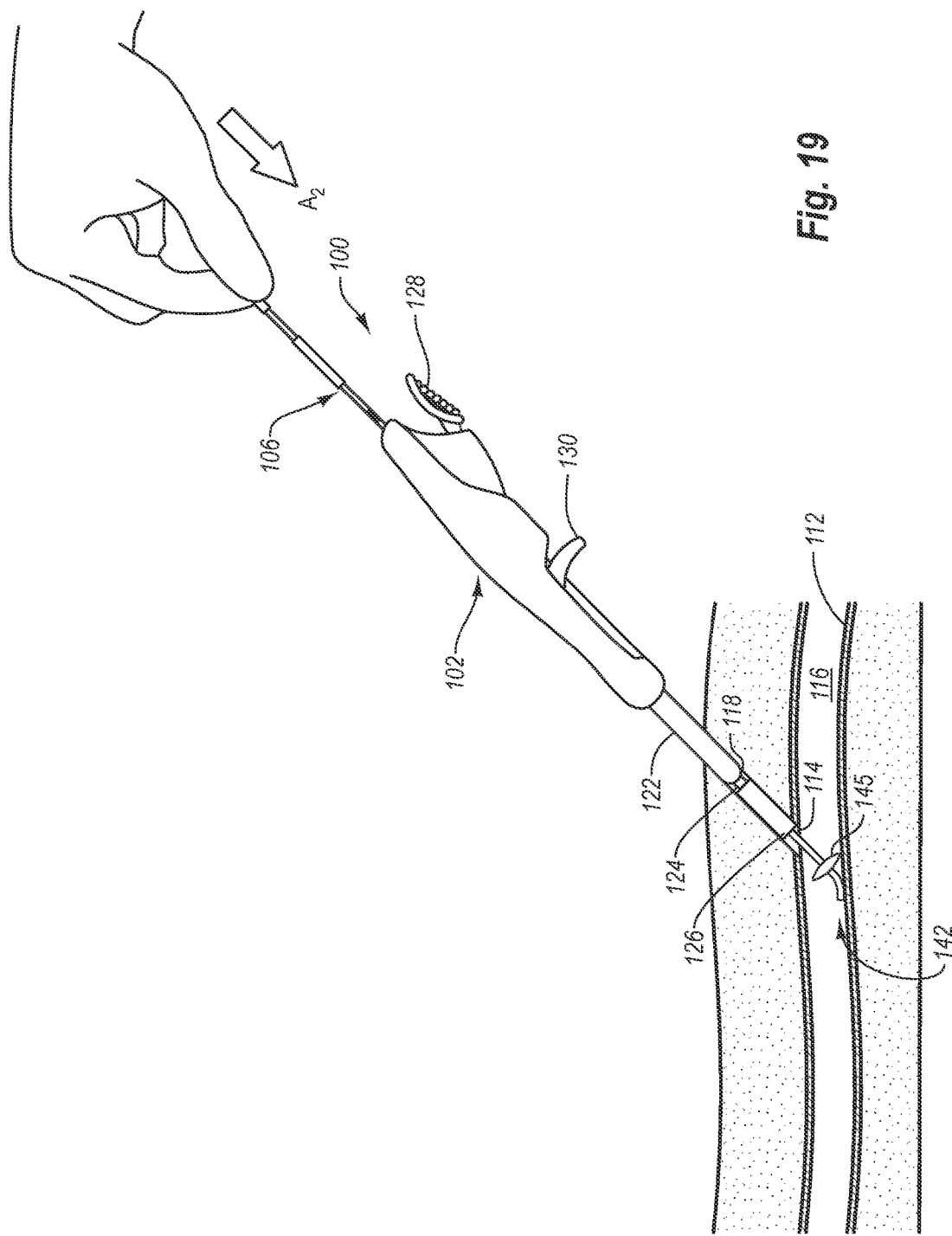
FIG. 19 is a side view of the tissue puncture treatment assembly of FIG. 18 with the locator wire assembly advanced distally to separate the expandable portion from the vessel wall.

Referring now to FIG. 18, the wire locking member 128 is released so that the sealing pad delivery device 102 may be moved relative to the locator wire assembly 106. The locator wire assembly 106 is then advanced distally in the direction $A_2$ as shown in FIG. 19 until the expandable portion 145 is moved out of contact with an inner wall 115 of the vessel 112.

Figure 20:
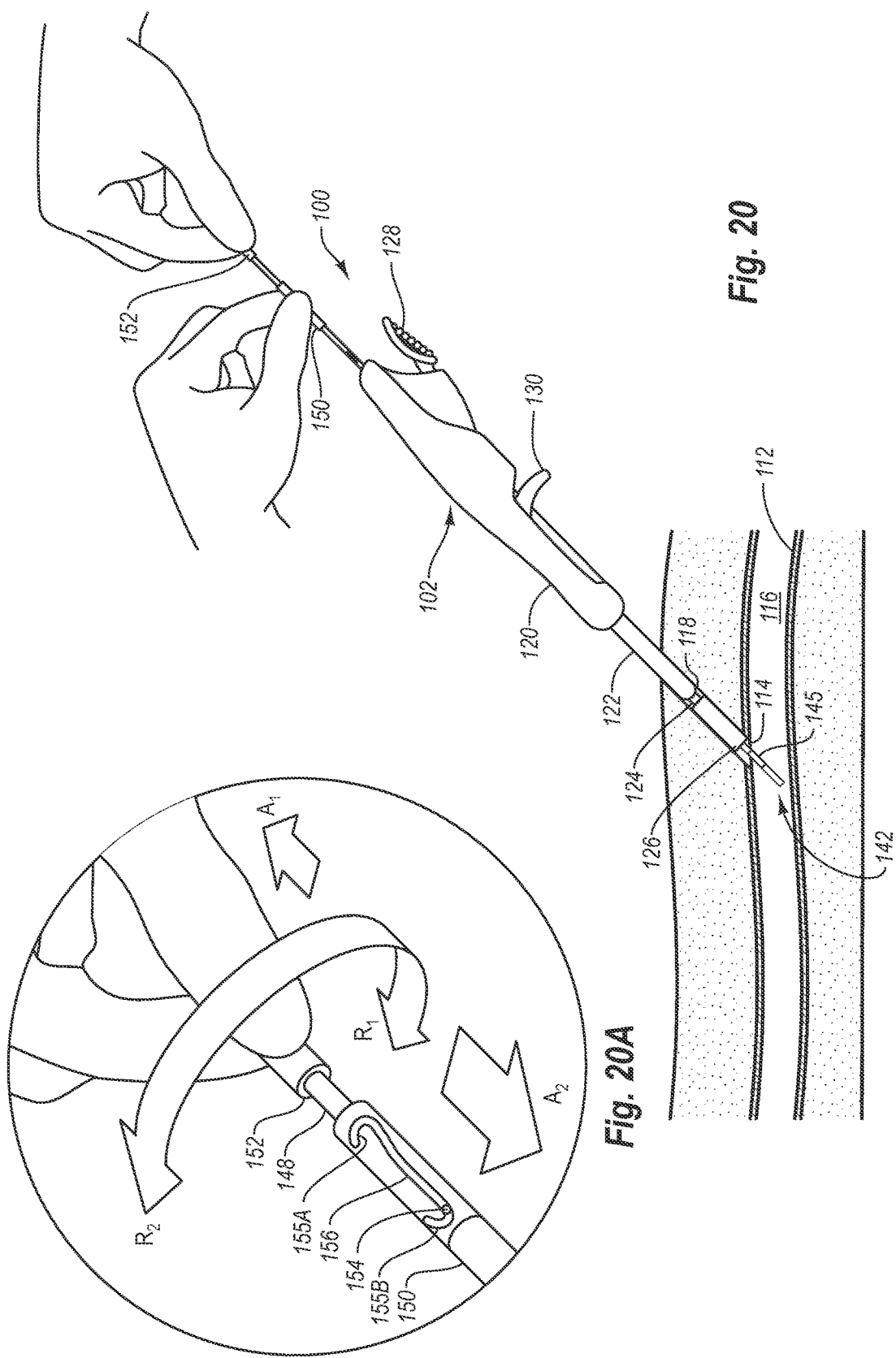

FIGS. 20 and 20A illustrate the expandable portion 145 moved into the unexpanded state after being spaced distally away from the vessel puncture 114. The operator rotates the filling member 148 relative to the locator tube 140 in the direction $R_1$ to move the follower member 154 out of locking portion 155B. The operator may then apply a force to the locator tube 140 in the distal direction $A_2$ via the first grasping member 150 while applying an opposite force to the filling member 148 in the proximal direction $A_1$ via the second grasping member 152. After the follower member 154 reaches a proximal end of the track 156, the operator rotates the filling member 148 in the direction $R_2$ to move the follower member 154 into the locking portion 155A. The maximum width dimension of the expandable portion 145 is reduced from a size $D_2$ to a size that is smaller than the maximum dimension of the vessel puncture 114 (e.g., the dimension $D_1$ shown in FIG. 1).

Figure 21:
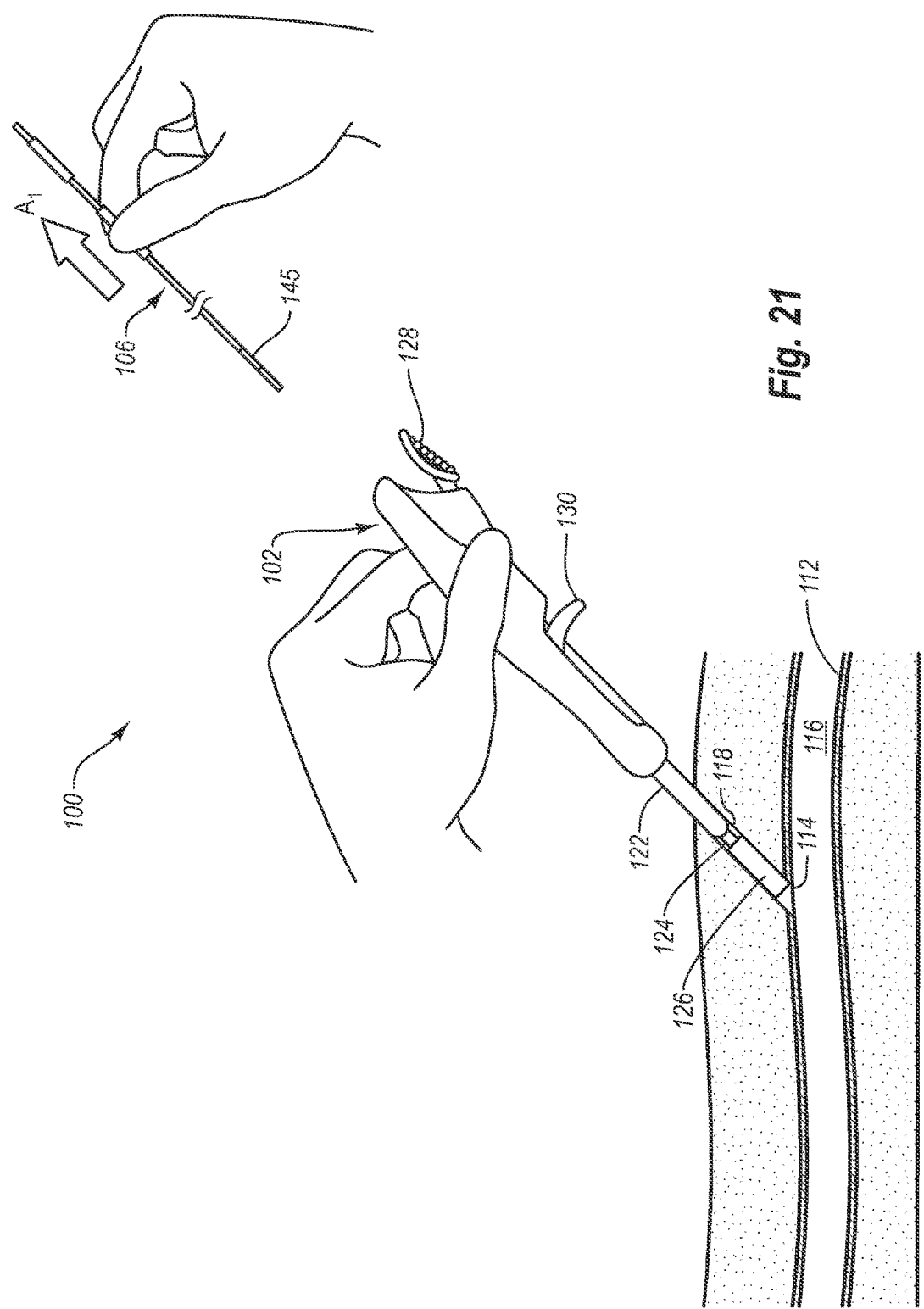
FIG. 21 is a side view of the tissue puncture treatment assembly of FIG. 20 with the locator wire assembly being retracted through the sealing pad and removed from the sealing pad delivery device.

Referring to FIG. 21, the locator wire assembly 106 is retracted proximally in the direction $A_1$ out of the vessel 112, through the sealing pad 126, and out of the sealing pad delivery device 102 while holding the sealing pad delivery device 102 in a fixed position relative to the vessel 112.

Referring to FIG. 22, the sealing delivery device 102 is retracted proximally in the direction $A_1$ out of the percutaneous incision 118. The sealing pad 126 is left behind within the percutaneous incision 118 at a position adjacent the vessel puncture 114. Typically the sealing pad 126 comprises an expandable material that expands to fill the percutaneous incision 118 at a location adjacent to the vessel puncture 114. In at least one example, the sealing pad 126 comprises a collagen material. The sealing pad 126 is typically configured to provide hemostasis for the vessel puncture 114.

Many other constructions are possible for the various features of the tissue puncture treatment assembly 100 described above with reference to the attached figures. In particular, the aspects of the locator wire assembly 106 including various arrangements for the expandable portion 145 and filling member 148 described above may be changed or modified in accordance with the teachings provided herein.

The preceding description has been presented only to illustrate and describe exemplary embodiments of the present disclosure. It is not intended to be exhaustive or to limit the invention to any precise form disclosed. Many modifications and variations are possible in light of the above teaching. It is intended that the scope of the invention be defined by the following claims.

What is claimed is:

1. A tissue puncture locator device, comprising:
   an anchor assembly, including:
   a tube portion;
   an anchor portion positioned at a distal end of the tube portion and configured for placement through a vascular incision into a vessel, the anchor portion having an unexpanded configuration that permits passage through the vascular incision and an expanded configuration that limits passage through the vascular incision;
   a filling member retained in the tube portion and adapted for insertion from the tube portion into the anchor portion to provide the expanded configuration, and adapted for retraction from the anchor portion into the tube portion to provide the unexpanded configuration, the filling member having a random contorted shape configuration collected within the anchor portion, a distal tip of the filling member being movable through a plurality of random proximally and distally extending paths while filling the anchor portion;
   a sealing member configured for placement adjacent the vascular incision outside the vessel, the anchor portion being retractable through the sealing member when in the unexpanded configuration.

2. The tissue puncture locator device of claim 1, wherein the filling member is selected from a group consisting of a wire member, a polymer strand, and a gel strand.

3. The tissue puncture locator device of claim 1, further comprising a handle portion, the tube portion extending from the handle portion to the anchor portion.

4. The tissue puncture locator device of claim 1, wherein the sealing member is movable along the tube portion to the placement adjacent the vascular incision.

5. The tissue puncture locator device of claim 1, wherein the sealing member comprises a collagen material.

6. The tissue puncture locator device of claim 1, wherein the anchor assembly further includes an actuator configured to move the filling member into the anchor portion and retract the filling member from the anchor portion.

7. A tissue puncture locator device, comprising:
   an anchor assembly, including:
   a tube portion having a first portion and a second portion, the first portion having a first tubular wall thickness and the second portion having a second tubular wall thickness, the second wall thickness being reduced relative to the first wall thickness, the second portion positioned at a distal end of the tube portion and configured for placement through a vascular incision into a vessel, the second portion having an unexpanded configuration that permits passage of the second portion through the vascular incision and an expanded configuration that limits passage through the vascular incision;
   a filling member retained in the first portion of the tube portion and adapted for insertion from the first portion into the second portion to provide the expanded configuration, the filling member adapted for retraction from the second portion into the first portion to provide the unexpanded configuration, the filling member having a random contorted shape configuration collected within the second portion, a distal tip of the filling member being configured to randomly move proximally and distally within the second portion when filling the second portion;
   a sealing member configured for placement adjacent the vascular incision outside the vessel, the second portion of the tube portion being retractable through the sealing member when in the unexpanded configuration.

8. The tissue puncture locator device of claim 7, wherein the anchor assembly further includes an actuator configured to move the filling member into the second portion and to retract the filling member from the second portion.

9. The tissue puncture locator device of claim 7, wherein the filling member is configured to assume various shapes upon each insertion from the first portion into the second portion.

10. The tissue puncture locator device of claim 7, wherein the first portion has an inner diameter and the filling member has an outer diameter, the inner diameter being sized between about 100 and about 200 percent of the outer diameter.

11. A tissue puncture locator device, comprising:
    an anchor assembly, including:
    a tube portion;
    an anchor member positioned at a distal end of the tube portion and configured for placement through a vascular incision into a vessel, the anchor member having an unexpanded configuration that permits passage through the vascular incision and an expanded configuration that limits passage through the vascular incision;
- a filling member retained in the tube portion in a straight configuration and adapted for insertion from the tube portion into a randomly expanded and collected shape in the anchor member to provide the expanded configuration, a distal end of the filling member being movable through a random proximal and distal movement to reach the expanded configuration, and adapted for retraction from the randomly expanded shape in the anchor member to the straight configuration in the tube portion to provide the unexpanded configuration;
- a sealing member configured for placement adjacent the vascular incision outside the vessel, the anchor member being retractable through the sealing member when in the unexpanded configuration.

12. The tissue puncture locator device of claim 11, wherein the anchor assembly further includes an actuator configured to move the filling member into the anchor member and to retract the filling member from the anchor member.

13. The tissue puncture locator device of claim 11, wherein the filling member is configured to assume various different shapes upon each insertion from the tube portion into the anchor member.

14. The tissue puncture locator device of claim 11, wherein the tube portion has an inner diameter and the filling member has an outer diameter, the inner diameter being sized between about 100 and about 200 percent of the outer diameter.

15. A tissue puncture locator device, comprising:
an anchor assembly, including:
- a tube portion having a first portion and a second portion, the first portion having a first tubular wall thickness and the second portion having a second tubular wall thickness, the second wall thickness being reduced relative to the first wall thickness, the second portion positioned at a distal end of the tube portion and configured for placement through a vascular incision into a vessel, the second portion having an unexpanded configuration that permits passage of the second portion through the vascular incision and an expanded configuration that limits passage through the vascular incision;
- a filling member retained in the first portion of the tube portion and adapted for insertion from the first portion into the second portion to provide the expanded configuration, the filling member adapted for retraction from the second portion into the first portion to provide the unexpanded configuration, the filling member having a random contorted shape configuration within the second portion;
- a sealing member configured for placement adjacent the vascular incision outside the vessel, the second portion of the tube portion being retractable through the sealing member when in the unexpanded configuration;
- wherein the first portion has an inner diameter and the filling member has an outer diameter, the inner diameter being sized between about 100 and about 200 percent of the outer diameter.

16. A tissue puncture locator device, comprising:
an anchor assembly, including:
- a tube portion;
- an anchor member positioned at a distal end of the tube portion and configured for placement through a vascular incision into a vessel, the anchor member having an unexpanded configuration that permits passage through the vascular incision and an expanded configuration that limits passage through the vascular incision;
- a filling member retained in the tube portion in a straight configuration and adapted for insertion from the tube portion into a randomly expanded shape in the anchor member to provide the expanded configuration, and adapted for retraction from the randomly expanded shape in the anchor member to the straight configuration in the tube portion to provide the unexpanded configuration;
- a sealing member configured for placement adjacent the vascular incision outside the vessel, the anchor member being retractable through the sealing member when in the unexpanded configuration;
- wherein the tube portion has an inner diameter and the filling member has an outer diameter, the inner diameter being sized between about 100 and about 200 percent of the outer diameter.

\* \* \* \* \*